United States Patent
Ahn et al.

(10) Patent No.: US 10,793,889 B2
(45) Date of Patent: Oct. 6, 2020

(54) METHOD OF PACKING POLYNUCLEOTIDES

(71) Applicant: KOREA INSTITUTE OF SCIENCE AND TECHNOLOGY, Seoul (KR)

(72) Inventors: Dae Ro Ahn, Seoul (KR); Kyoung Ran Kim, Seoul (KR)

(73) Assignee: KOREA INSTITUTE OF SCIENCE AND TECHNOLOGY, Seoul (KR)

(*) Notice: Subject to any disclaimer, the term of this patent is extended or adjusted under 35 U.S.C. 154(b) by 437 days.

(21) Appl. No.: 15/444,605

(22) Filed: Feb. 28, 2017

(65) Prior Publication Data

US 2018/0105852 A1    Apr. 19, 2018

(30) Foreign Application Priority Data

Oct. 13, 2016  (KR) .................. 10-2016-0132850

(51) Int. Cl.
  *C12P 19/34*    (2006.01)
  *C12N 15/115*   (2010.01)
  *C12N 15/87*    (2006.01)

(52) U.S. Cl.
  CPC ............ *C12P 19/34* (2013.01); *C12N 15/115* (2013.01); *C12N 15/87* (2013.01); *C12N 2310/16* (2013.01); *C12N 2310/335* (2013.01); *C12N 2310/3523* (2013.01); *C12N 2310/53* (2013.01); *C12N 2330/50* (2013.01)

(58) Field of Classification Search
  CPC ....................................................... C12P 19/34
  See application file for complete search history.

(56) References Cited

U.S. PATENT DOCUMENTS

| 2012/0263648 A1* | 10/2012 | Shapiro ............... B82Y 5/00 424/9.1 |
| 2013/0156849 A1* | 6/2013 | de Fougerolles ...... A61K 48/00 424/450 |
| 2016/0244501 A1* | 8/2016 | Ellsworth ............ C07K 14/705 |

OTHER PUBLICATIONS

Marcel Hollenstein, Generation of long, fully modified, and serum-resistant oligonucleotides by rolling circle amplification, Org. Biomol. Chem., Aug. 7, 2015, pp. 9820-9824, vol. 13.
Communications of Korean Office Action dated Aug. 18, 2017 of Korean Patent Application No. 10-2016-0132850, which corresponds to this application.

* cited by examiner

*Primary Examiner* — Jezia Riley
(74) *Attorney, Agent, or Firm* — Goldilocks Zone IP Law

(57) ABSTRACT

Provided is a method of preparing nanoparticle-type polynucleotides, the method comprising forming the polynucleotides comprising modified nucleotides, in which the forming includes chemically synthesizing the polynucleotides comprising modified nucleotides, synthesizing the polynucleotides comprising modified nucleotides using an enzyme, or a combination thereof.

13 Claims, 5 Drawing Sheets
Specification includes a Sequence Listing.

SEQUENCE LISTING

<160> NUMBER OF SEQ ID NOS: 7

<210> SEQ ID NO 1
<211> LENGTH: 20
<212> TYPE: DNA
<213> ORGANISM: Artificial Sequence
<220> FEATURE:
<223> OTHER INFORMATION: RCA primer

<400> SEQUENCE: 1
ctctggtgag gacaggactt                                                 20

<210> SEQ ID NO 2
<211> LENGTH: 79
<212> TYPE: DNA
<213> ORGANISM: Artificial Sequence
<220> FEATURE:
<223> OTHER INFORMATION: Template 1

<400> SEQUENCE: 2
ctcaccagag aaaaaaaaaa aaaaaaaaaa aaaaaaaaaa aaaaaaaaaa aaaaaaaaaa     60
aaaaaaaaaa agtcctgtc                                                  79

<210> SEQ ID NO 3
<211> LENGTH: 79
<212> TYPE: DNA
<213> ORGANISM: Artificial Sequence
<220> FEATURE:
<223> OTHER INFORMATION: P1

<400> SEQUENCE: 3
gacaggactt tttttttttt tttttttttt tttttttttt tttttttttt tttttttttt     60 ttttttttc tctggtgag                                                   79

<210> SEQ ID NO 4
<211> LENGTH: 75
<212> TYPE: DNA
<213> ORGANISM: Artificial Sequence
<220> FEATURE:
<223> OTHER INFORMATION: Template 2

<400> SEQUENCE: 4
ctcaccagag ccgcatgcca tccgcccagt tgacaaaaaa accgcatgcc atccgcccag     60
ttgacaagtc ctgtc                                                      75

<210> SEQ ID NO 5
<211> LENGTH: 75
<212> TYPE: DNA
<213> ORGANISM: Artificial Sequence
<220> FEATURE:
<223> OTHER INFORMATION: P2

<400> SEQUENCE: 5
gacaggactt gtcaactggg cggatggcat gcggtttttt tgtcaactgg gcggatggca     60
tgcggctctg gtgag                                                      75

<210> SEQ ID NO 6
<211> LENGTH: 79
<212> TYPE: DNA
<213> ORGANISM: Artificial Sequence
<220> FEATURE:
<223> OTHER INFORMATION: Template 3

<400> SEQUENCE: 6

```
ctcaccagag ccaccaccac caacaccacc accaccaaaa aaaccaccac caccaacacc      60
accaccacca agtcctgtc                                                   79
```

<210> SEQ ID NO 7
<211> LENGTH: 79
<212> TYPE: DNA
<213> ORGANISM: Artificial Sequence
<220> FEATURE:
<223> OTHER INFORMATION: P3

<400> SEQUENCE: 7

```
gacaggactt ggtggtggtg gtgttggtgg tggtggtttt tttggtggtg gtggtgttgg      60
tggtggtggc tctggtgag                                                   79
```

METHOD OF PACKING POLYNUCLEOTIDES

CROSS-REFERENCE TO RELATED APPLICATION

This application claims the benefit of Korean Patent Application No. 10-2016-0132850, filed on Oct. 13, 2016, in the Korean Intellectual Property Office, the disclosure of which is incorporated herein in its entirety by reference.

BACKGROUND

1. Field

The present disclosure relates to a method of packing polynucleotides, which is used for stably storing the polynucleotides, increasing transfection efficiency thereof, or increasing intracellular delivery efficiency of polynucleotide nanoparticles to adopt the polynucleotide nanoparticles as drug carriers.

2. Description of the Related Art

Polynucleotides including DNA and RNA are genetic materials produced in cells, and function to pass a variety of traits of living things to subsequent generations. Further, polynucleotides are materials performing a variety of biological functions, comprising storing codes needed for protein expression and performing enzymatic functions as they are. In vitro as well as in vivo, polynucleotides may be prepared by a polymerase or an oligonucleotide synthesizer to form genomic DNA, antisense oligonucleotides, mRNA, siRNA, microRNA, sgRNA, or aptamers having biochemical functions. Polynucleotides may be used for biochemical activity, but polynucleotides themselves may also form various structures by self-assembly. Based on these structural characteristics, polynucleotides may be applied to materials that perform useful functions (e.g., drug carriers, chips, logic circuits, etc.). In some cases, polynucleotides extracted from cells are required to be stored outside cells for additional analysis. Outside cells, nucleotides may be readily damaged or degraded, because of a lack of intracellular materials binding to and protecting nucleotides (e.g., histone proteins, RNA binding proteins, etc.). To prevent this, a method of using a material capable of binding to nucleotides and protecting the nucleotides from environmental damage to the nucleotides or a method of preventing degradation or damage of the nucleotides by self-packing of the nucleotides into a more stable structure may be considered. Of these methods, the self-packing method is very useful, because it may be applied to controlling the above-mentioned structures or sizes of various polynucleotides which are formed outside cells, as well as to storing genetic materials. A recently known technique for packing polynucleotides is a method of controlling sizes of polynucleotides by varying the concentration of a polymerase which polymerizes nucleotides.

SUMMARY

An aspect of the invention provides a method of preparing nanoparticle-type polynucleotides, the method comprising forming the polynucleotides comprising modified nucleotides, in which the forming includes chemically synthesizing the polynucleotides comprising modified nucleotides, synthesizing the polynucleotides comprising modified nucleotides using an enzyme, or a combination thereof.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
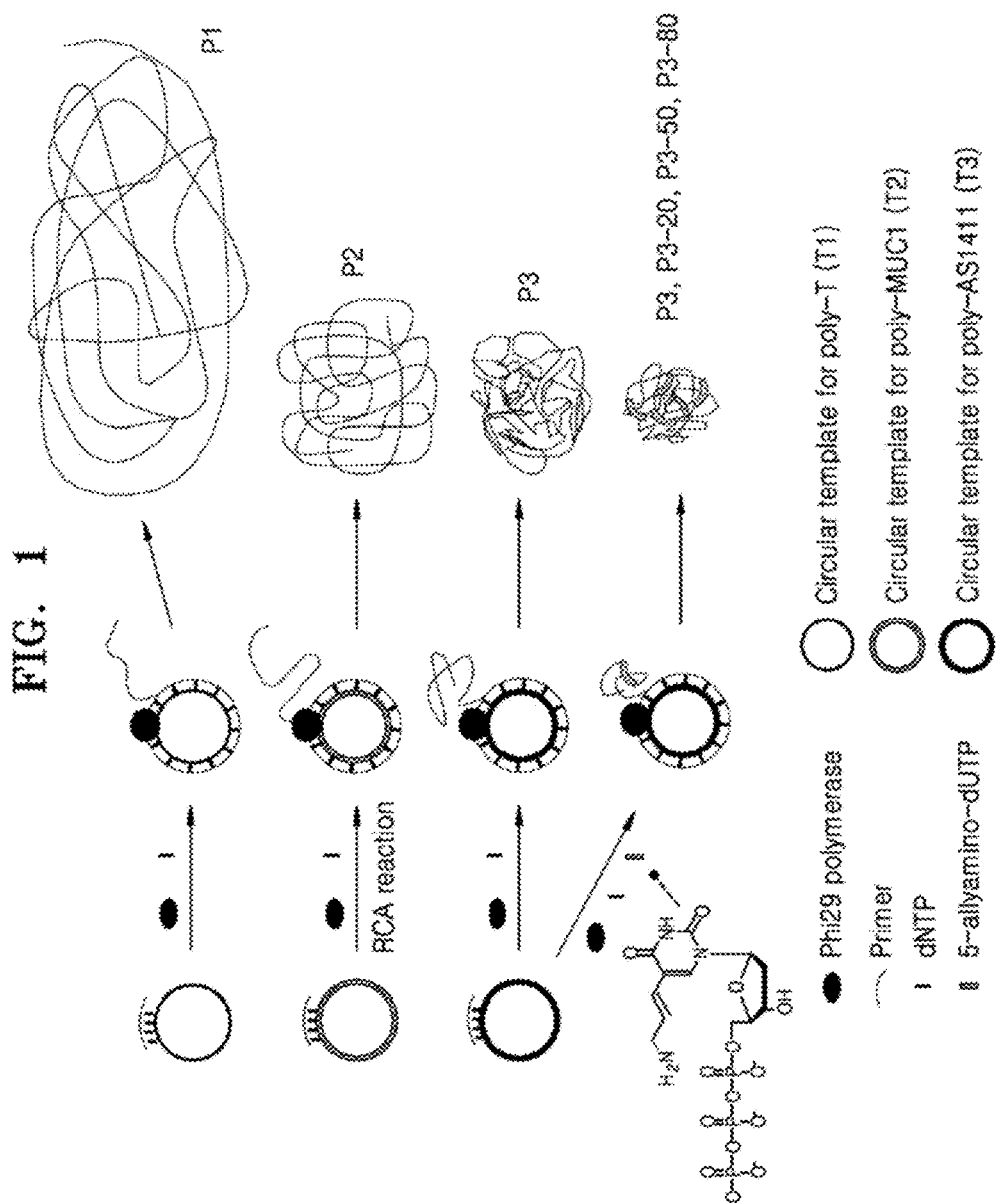
FIG. 1 shows a schematic representation of the fabrication of size-controlled RCA products by using secondary structure-forming sequences and 5-allylamino-dUTP.

An aspect of the invention provides a method of preparing nanoparticle-type polynucleotides, the method comprising forming the polynucleotides comprising modified nucleotides, in which the forming comprises chemically synthesizing the polynucleotides comprising modified nucleotides, synthesizing the polynucleotides comprising modified nucleotides using an enzyme, or a combination thereof.

The term 'nucleotides' refer to either deoxyribonucleotides or ribonucleotides, and unless otherwise specified, the nucleotides may include natural nucleotide analogs and modified nucleotide analogs of which sugar or base moieties are modified. The term 'polynucleotides' may have the same meaning as 'oligonucleotides', and the polynucleotides mean polymers of the nucleotides and may include single- or double-stranded forms.

The term 'modified' means that particular moieties of what exists in nature are manipulated, and for example, the 'modified nucleotides' refer to nucleotides, in which an element or a residue at a particular position of each of three components constituting nucleotides, that is, a five-carbon sugar, a phosphate group, and a base is replaced with another element, residue, or functional group.

The nanoparticles of the present inventive concept may be formed by self-assembly of the nucleotides comprising the modified nucleotides by interactions between the nucleotides such as electrical attractions between cations and anions thereof. The modified nucleotides may be incorporated into the polynucleotides in a predetermined pattern. The pattern may be repeated insertion or substitution of the modified nucleotides into a particular nucleotide sequence, construction of a particular nucleotide sequence at least partially consisting of the modified nucleotides, or local concentration of the modified nucleotides at a particular region of the polynucleotide, but is not limited thereto. A shape, density, or size of the nanoparticles formed by self-assembly may be controlled by varying a method of modifying the modified nucleotides, a number or pattern of the modified nucleotides in the polynucleotides, etc.

In some embodiments, the nanoparticles may have a predetermined size. The term 'nanoparticles' refers to particles having a predetermined size of 1000 nm or less, but is not limited thereto. The size of the nanoparticles may be a diameter of 10 nm to 1000 nm, or 50 nm to 150 nm.

In some embodiments, chemically synthesizing the polynucleotides comprising the modified nucleotides may include synthesizing the polynucleotides by oligo synthesis. The term 'oligo synthesis' refers to chemical synthesis of nucleotide fragments having a chemical structure of a defined sequence, which may be conducted at a small-scale laboratory level, or at a large, industrial scale by an oligonucleotide synthesizer known in the art. In detail, the oligo synthesis may include H-phosphonate synthesis, phosphodiester synthesis, phosphotriester synthesis, phosphite triester synthesis, or a combination thereof, but is not limited thereto.

In some embodiments, synthesizing the polynucleotide comprising the modified nucleotides using an enzyme may be a method comprising extending a primer by incubating a reaction mixture comprising a template nucleotide, a polymerase, modified-NTP (nucleoside triphosphate), and the primer having a sequence at least partially complementary to the template; and amplifying polynucleotides at least partially comprising the modified nucleotides, in which the modified-NTP may be one or more selected from the group consisting of modified-ATP, modified-TTP, modified-CTP, modified-GTP, and modified-UTP.

In order to amplify the polynucleotide, the template may include a primer binding site and an appropriate nucleotide sequence to produce a desired polynucleotide. Therefore, a shape of the template may vary depending on the primer sequence to be used or the nucleotide sequence of the desired polynucleotide.

The term 'primer' refers to a sequence of 15 to 35 nucleotides having a free 3' hydroxyl group, which forms base pairs with a complementary nucleotide template and serves as a starting point for replication of the nucleotide template. The primer may initiate DNA synthesis in an appropriate buffer at an appropriate temperature in the presence of reagents for polymerization using DNA polymerase or reverse transcriptase, and four different nucleotide triphosphates.

The term 'polymerase' refers to an enzyme that synthesizes long chains or polymers of nucleotides. When the polymerase is DNA polymerase, it may be selected from the group consisting of E. coli DNA polymerase I, Klenow fragment, phi29 DNA polymerase, vent DNA polymerase, T4, T7 DNA polymerase, and Taq polymerase. When the polymerase is RNA polymerase, it may be selected from the group consisting of RNA polymerase I, RNA polymerase II, RNA polymerase III, and T7 RNA polymerase. Further, the polymerase may be terminal deoxynucleotidyl transferase (TdT) or reverse transcriptase.

The 'NTP' of the present inventive may refer to a plurality of NTPs, and may include dNTP (deoxyribonucleoside triphosphate) or rNTP (ribonucleoside triphosphate). The term 'modified-NTP' may refer to NTP produced by manipulating a particular moiety of what exists in nature (naturally occurring) NTP. The 'modified' means that an element or a residue at a particular position of each of three components constituting a basic chemical structure of NTP, that is, a 5-carbon sugar, a phosphate group, and a base is replaced with another element, residue, or functional group.

Naturally occurring NTP has a structure, in which three phosphate groups bind to a nucleoside composed of a base (also termed a nitrogenous base, a nucleobase, or a base including adenine, guanine, thymine, or cytosine) and a five-carbon sugar, the five-carbon sugar including either ribose or deoxyribose, and as the five-carbon sugar of NTP, rNTP having ribose and dNTP having deoxyribose. Therefore, when NTP is rNTP, the NTP may include particularly ATP, TTP (or $m^5$UTP), CTP, GTP, and UTP, and when NTP is dNTP, the NTP may include particularly dATP, dTTP, dCTP, dGTP, and dUTP.

The term 'extending' means synthesizing, by action of the polymerase, a chain or a polymer composed of nucleotides by linking nucleotides (NTP or modified-NTP) from the primer, and the term 'incubating' means making conditions under which the polymerase functions to extend the primer so that an activation reaction of the polymerase occurs. For example, when the polymerase is phi29 DNA polymerase, the incubating means that a reaction mixture containing the nucleotides (NTP or modified-NTP), the primer, the phi29 DNA polymerase, and a buffer solution (according to the manufacturer's instructions) suitable for activation of the polymerase may be left at 37° C. for 1 hour. Therefore, the conditions may vary depending on the kind of polymerase to be used in the method, a composition of nucleotides (e.g., a ratio of NTP and modified-NTP, when they are mixed), a length of the primer, a nucleotide sequence composition of the primer, a nucleotide sequence composition of the template, and a length, a quantity, or a composition of polynucleotides to be produced, etc.

When a reaction mixture containing a combination of NTP and modified-NTP is subjected to the 'incubating', polynucleotides produced from the reaction mixture may at least partially compose modified-NTP. If necessary, a ratio of NTP and modified-NTP in the reaction mixture may be adjusted, and as a result, the ratio of NTP and modified-NTP in the produced polynucleotides may vary.

The term 'amplifying' means that a start polynucleotide or a polynucleotide produced by a single reaction is replicated numerously or exponentially by repeated reactions, and may be conducted by a method selected from the group consisting of primer extension, rolling circle amplification, rolling circle transcription, in vitro transcription, polymerase chain reaction, and nucleotide terminal transferase reaction.

In some embodiments, the template nucleotide may be DNA or RNA. A DNA template (that is, the template nucleotide is DNA) may be used to produce an RNA strand (in this case, the RNA strand may be mRNA) through transcription by polymerase (RNA polymerase II in humans) or to produce a DNA strand through replication by DNA polymerase. Further, an RNA template (that is, the template nucleotide is RNA) may be used to replicate RNA through replication by RNA-dependent RNA polymerase. The replication using the RNA template may be achieved by an RNA virus (e.g., poliovirus) using the RNA-dependent RNA polymerase for the above-described replication process. A composition, shape (single-stranded, double-stranded, circular, or linear form, etc.) template or a nucleotide sequence of the DNA or RNA may vary depending on a kind and a sequence of a polynucleotide to be produced by the above method.

In another embodiment, the template nucleotide may be single-stranded or double-stranded. When the template nucleotide is double-stranded, the incubation conditions required for binding of the primer to the template nucleotide and activation of the polymerase may vary in the method of amplifying a desired polynucleotide for amplification of the polynucleotide. For example, when the template nucleotide is double-stranded DNA, and the incubation is polymerase chain reaction, a desired polynucleotide DNA may be amplified by a process comprising denaturing DNA to separate the double-stranded DNA into single-stranded DNAs; binding the template nucleotide with a primer which is at least partially complementary to the template nucleotide; and extending the primer by Taq polymerase. In this regard, the denaturing may include heating at 90° C. to 95° C., the binding may include cooling at 50° C. to 65° C., and the extending may include heating at 70° C. to 75° C., but the conditions of each step may vary depending on a length of the template nucleotide or a composition of the nucleotide sequence; a length of the primer, complementarity to the template nucleotide, or a composition of the nucleotide sequence; and a kind or efficiency of Taq polymerase. Further, when the template nucleotide is single-stranded, incubation conditions suitable for production of the desired polynucleotide by binding the polymerase to the template nucleotide may also vary depending on the length or kind of the template nucleotide and the composition or a characteristic of the nucleotide sequence.

In still another embodiment, the template nucleotide may be circular or linear. When the template nucleotide is circular, it may be, for example, a plasmid or a vector. With regard to incubation conditions used in the method of amplifying the polynucleotide, when the incubation is, for example, a polymerase reaction, the form of the template nucleotide to be used may vary depending on a kind of the polymerase reaction. For example, when the polymerase reaction is rolling circle amplification or polymerase chain reaction, the template nucleotide may be circular.

In some embodiments, the modified-NTPs or modified-dNTPs may be those in which one or more of the five-carbon sugar, the phosphate group, and the base are modified. Here, the term 'modified' means that an element or a residue at a particular position of the five-carbon sugar, the phosphate group, and the base is replaced with another element, residue, or functional group, as described above. The five-carbon sugar may be a naturally occurring five-carbon sugar and may include either ribose or deoxyribose. A modified-NTP having a modified five-carbon sugar may be, for example, a modified-NTP in which a hydroxyl group of the 2- or 3-carbon site (3-carbon site of the sugar in the case of modified-dNTP) of ribose or deoxyribose is replaced with another element, residue, or functional group. When the hydroxyl group of the 3-carbon site of ribose or deoxyribose is replaced with a particular small substituent (e.g., an allyl group), activity of DNA polymerase remains (Proc Natl Acad Sci USA. 2006, 103(52): 19635-19640). Therefore, even if modified-dNTPs are used, a polymerization reaction may be performed. The substituent to be used in the modification may vary. NTP has three phosphate groups, and a modified-NTP having a modified phosphate group may be, for example, a modified-NTP, in which one or more of three phosphate groups are replaced with another element, residue, or functional group. The base may be a purine base or a pyrimidine base. When the base is a purine base, the base may be adenine or guanine, and when the base is a pyrimidine base, the base may be thymine, uracil, or cytosine. Therefore, a modified-NTP having a modified base may be a modified-NTP, in which an element at a particular position of one or more of adenine, guanine, thymine, uracil, and cytosine is replaced with another element, residue, or functional group.

In some embodiments, the modified-NTP (or dNTP) may be a modified NTP having a modification of the hydrogen of the 8-carbon site of the purine ring when the base of the modified-NTP is adenine or guanine, a modified NTP having a modification of the hydrogen of the 5-carbon site of the pyrimidine ring when the base of the modified-NTP is cytosine or uracil, and a modified NTP having a modification of the methyl group of the 5-carbon site of the pyrimidine ring when the base of the modified-NTP is thymine. According to a previously known report, although bulky groups such as energy transfer dyes bind to the 8-carbon site of the purine ring of adenine or guanine and the 5-carbon site of the pyrimidine ring of thymine or cytosine, polymerization activity of DNA polymerase remains (Proc Natl Acad Sci USA. 2006, 103(52): 19635-19640). However, the modified-NTP (or dNTP) is not limited thereto, as long as the polymerase used in the polymerization reaction maintains its activity.

In some embodiments, the modification may be replacement with one or more selected from the group consisting of a cationic residue, an anionic residue, a neutral residue, a hydrophobic residue, and a hydrogen-binding residue. The term 'cationic residue' means a positively charged residue in an environment where polynucleotides exist (e.g., at pH 8.0 to 8.5 in the case of a buffer used in PCR), and may be exemplified by an amine residue. The term 'anionic residue' also means a negatively charged residue in the environment where polynucleotides exist, as described above, and may be exemplified by a carboxyl group. The term 'neutral residue' means a residue that induces dipoles but has no charge in the environment where polynucleotides exist, and may be exemplified by diethylthioether. The term 'hydrophobic residue' means a residue having no affinity for water, and may be exemplified by an alkyl group or a benzene ring. The term 'hydrogen-binding residue' means a residue capable of forming a hydrogen bond, and may be exemplified by a hydroxyl group, etc.

In some embodiments, the cationic residue may be a substituted or unsubstituted $C_1$-$C_{30}$ alkyl group, a substituted or unsubstituted $C_1$-$C_{30}$ alkenyl group, a substituted or unsubstituted $C_1$-$C_{30}$ alkynyl group, a substituted or unsubstituted $C_1$-$C_{30}$ cycloalkyl group, a substituted or unsubstituted $C_5$-$C_{30}$ aryl group, a substituted or unsubstituted $C_5$-$C_{30}$ arylalkyl group, a substituted or unsubstituted $C_5$-$C_{30}$ arylalkenyl group, a substituted or unsubstituted $C_5$-$C_{30}$ arylalkynyl group, a substituted or unsubstituted $C_5$-$C_{30}$ heteroaryl group, a substituted or unsubstituted $C_1$-$C_{30}$ heterocyclyl group, a substituted or unsubstituted $C_1$-$C_{30}$ heterocycloalkyl group, a substituted or unsubstituted $C_1$-$C_{30}$ heterocyclylalkyl group, a substituted or unsubstituted $C_5$-$C_{30}$ heteroarylalkyl group, a substituted or unsubstituted $C_5$-$C_{30}$ heteroarylalkenyl group, or a substituted or unsubstituted $C_5$-$C_{30}$ heteroarylalkynyl group, which is substituted with one or more selected from the group consisting of amine (ammonium), guanidine (guanidinium), pyridine (pyridinium), and imidazole (imidazolium).

In some embodiments, the anionic residue may be a substituted or unsubstituted $C_1$-$C_{30}$ alkyl group, a substituted or unsubstituted $C_1$-$C_{30}$ alkenyl group, a substituted or unsubstituted $C_1$-$C_{30}$ alkynyl group, a substituted or unsubstituted $C_1$-$C_{30}$ cycloalkyl group, a substituted or unsubstituted $C_5$-$C_{30}$ aryl group, a substituted or unsubstituted $C_5$-$C_{30}$ arylalkyl group, a substituted or unsubstituted $C_5$-$C_{30}$ arylalkenyl group, a substituted or unsubstituted $C_5$-$C_{30}$ arylalkynyl group, a substituted or unsubstituted $C_5$-$C_{30}$ heteroaryl group, a substituted or unsubstituted $C_1$-$C_{30}$ heterocyclyl group, a substituted or unsubstituted $C_1$-$C_{30}$ heterocycloalkyl group, a substituted or unsubstituted $C_1$-$C_{30}$ heterocyclylalkyl group, a substituted or unsubstituted $C_5$-$C_{30}$ heteroarylalkyl group, a substituted or unsubstituted $C_5$-$C_{30}$ heteroarylalkenyl group, a substituted or unsubstituted $C_5$-$C_{30}$ heteroarylalkynyl group, a substituted or unsubstituted $C_1$-$C_{30}$ alkylamide group, a substituted or unsubstituted $C_1$-$C_{30}$ hydroxyalkyl group, a substituted or unsubstituted alkoxy group, a substituted or unsubstituted $C_1$-$C_{30}$ alkylamino group, a substituted or unsubstituted phenylamino group, a substituted or unsubstituted carbamoyl group, a substituted or unsubstituted oxadiazole group, or a substituted or unsubstituted carbamic acid group, which is substituted with one or more carboxylic acids (carboxylates).

In some embodiments, the neutral residue may be a substituted or unsubstituted $C_1$-$C_{30}$ alkyl group, a substituted or unsubstituted $C_1$-$C_{30}$ alkenyl group, a substituted or unsubstituted $C_1$-$C_{30}$ alkynyl group, a substituted or unsubstituted $C_1$-$C_{30}$ cycloalkyl group, a substituted or unsubstituted $C_5$-$C_{30}$ aryl group, a substituted or unsubstituted $C_5$-$C_{30}$ arylalkyl group, a substituted or unsubstituted $C_5$-$C_{30}$ arylalkenyl group, a substituted or unsubstituted $C_5$-$C_{30}$ arylalkynyl group, a substituted or unsubstituted $C_5$-$C_{30}$ heteroaryl group, a substituted or unsubstituted $C_1$-$C_{30}$ heterocyclyl group, a substituted or unsubstituted $C_1$-$C_{30}$ heterocycloalkyl group, a substituted or unsubstituted $C_1$-$C_{30}$ heterocyclylalkyl group, a substituted or unsubstituted $C_5$-$C_{30}$ heteroarylalkyl group, a substituted or unsubstituted $C_5$-$C_{30}$ heteroarylalkenyl group, a substituted or unsubstituted $C_5$-$C_{30}$ heteroarylalkynyl group, a substituted or unsubstituted $C_1$-$C_{30}$ alkylamide group, a substituted or unsubstituted $C_1$-$C_{30}$ hydroxyalkyl group, or a substituted or unsubstituted $C_1$-$C_{30}$ alkoxy group, which is substituted with one or more selected from the group consisting of a hydroxyl group, a halogen, an amide group, urea, a carbonyl group, a carbamate group, an imide group, a thiocarbamate group, a carbonate group, an ester, a thioester, a thiourea group, an imine group, and an enamine group.

In some embodiments, the hydrophobic residue may be selected from the group consisting of a substituted or unsubstituted $C_1$-$C_{30}$ alkyl group, a substituted or unsubstituted $C_1$-$C_{30}$ alkenyl group, a substituted or unsubstituted $C_1$-$C_{30}$ alkynyl group, a substituted or unsubstituted $C_1$-$C_{30}$ cycloalkyl group, a substituted or unsubstituted $C_5$-$C_{30}$ aryl group, a substituted or unsubstituted $C_5$-$C_{30}$ arylalkyl group, a substituted or unsubstituted $C_5$-$C_{30}$ arylalkenyl group, or a substituted or unsubstituted $C_5$-$C_{30}$ arylalkynyl group.

In some embodiments, the hydrogen-binding residue may be a substituted or unsubstituted $C_1$-$C_{30}$ alkyl group, a substituted or unsubstituted $C_1$-$C_{30}$ alkenyl group, a substituted or unsubstituted alkynyl group or unsubstituted $C_1$-$C_{30}$ cycloalkyl group, a substituted or unsubstituted $C_5$-$C_{30}$ aryl group, a substituted or unsubstituted $C_5$-$C_{30}$ arylalkyl group, a substituted or unsubstituted $C_5$-$C_{30}$ arylalkenyl group, a substituted or unsubstituted $C_5$-$C_{30}$ arylalkynyl group, a substituted or unsubstituted $C_5$-$C_{30}$ heteroaryl group, a substituted or unsubstituted $C_1$-$C_{30}$ heterocyclyl group, a substituted or unsubstituted $C_1$-$C_{30}$ heterocycloalkyl group, a substituted or unsubstituted $C_1$-$C_{30}$ heterocyclylalkyl group, a substituted or unsubstituted $C_5$-$C_{30}$ heteroarylalkyl group, a substituted or unsubstituted $C_5$-$C_{30}$ heteroarylalkenyl group, a substituted or unsubstituted $C_5$-$C_{30}$ heteroarylalkynyl group, a substituted or unsubstituted $C_1$-$C_{30}$ alkylamide group, a substituted or unsubstituted $C_1$-$C_{30}$ hydroxyalkyl group, a substituted or unsubstituted $C_1$-$C_{30}$ alkoxy group, a substituted or unsubstituted $C_1$-$C_{30}$ alkylamino group, a substituted or unsubstituted phenylamino group, a substituted or unsubstituted carbamoyl group, a substituted or unsubstituted oxadiazole group, or a substituted or unsubstituted carbamic acid group, which is substituted with one or more selected from the group consisting of a hydroxyl group, a halogen, an amide group, urea, a carbonyl group, a carbamate group, an imide group, a thiocarbamate group, a carbonate group, an ester, a thioester, a thiourea group, an imine group, and an enamine.

In the substituted or unsubstituted $C_1$-$C_{30}$ alkyl group, the substituted or unsubstituted $C_1$-$C_{30}$ alkenyl group, the substituted or unsubstituted $C_1$-$C_{30}$ alkynyl group, the substituted or unsubstituted $C_1$-$C_{30}$ cycloalkyl group, the substituted or unsubstituted $C_5$-$C_{30}$ aryl group, the substituted or unsubstituted $C_5$-$C_{30}$ arylalkyl group, the substituted or unsubstituted $C_5$-$C_{30}$ arylalkenyl group, the substituted or unsubstituted $C_5$-$C_{30}$ arylalkynyl group, the substituted or unsubstituted $C_5$-$C_{30}$ heteroaryl group, the substituted or unsubstituted $C_1$-$C_{30}$ heterocyclyl group, the substituted or unsubstituted $C_1$-$C_{30}$ heterocycloalkyl group, the substituted or unsubstituted $C_1$-$C_{30}$ heterocyclylalkyl group, the substituted or unsubstituted $C_5$-$C_{30}$ heteroarylalkyl group, the substituted or unsubstituted $C_5$-$C_{30}$ heteroarylalkenyl group, the substituted or unsubstituted $C_5$-$C_{30}$ heteroarylalkynyl group, the substituted or unsubstituted $C_1$-$C_{30}$ alkylamide group, the substituted or unsubstituted $C_1$-$C_{30}$ hydroxyalkyl group, the substituted or unsubstituted $C_1$-$C_{30}$ alkoxy group, the substituted or unsubstituted $C_1$-$C_{30}$ alkylamino group, the substituted or unsubstituted phenylamino group, the substituted or unsubstituted carbamoyl group, the substituted or unsubstituted oxadiazole group, or the substituted or unsubstituted carbamic acid group of the cationic residue, the anionic residue, the neutral residue, the hydrophobic residue, and the hydrogen-binding residue, the substituent may be selected from a halogen, a hydroxy group, a nitro group, a cyano group, an oxo group (=O), a thioxo group (=S), an azido group, a nitroso group, an amino group, a hydrazine group, a formyl group, an alkyl group, an alkoxy group, an aryl group, a haloalkyl group, a haloalkoxy group, an arylalkoxy group, a cycloalkyl group, an —O-cycloalkyl group, a heterocyclyl group, a heteroaryl group, an alkylamino group, an —O—CH$_2$-cycloalkyl group, —COOR$^a$, —C(O)R$^b$, —C(O)NR$^a$R$^b$, —NR$^a$C(O)NR$^b$R$^c$, —NR$^a$C(O)OR$^b$, —NR$^a$R$^b$, —NR$^a$C(O)R$^b$, —OR$^a$, —OR$^a$C(O)OR$^b$, —C(O)NR$^a$R$^b$, —OC(O)R$^a$, —R$^a$NR$^b$R$^c$, and —R$^a$OR$^b$; in which R$^a$, R$^b$, and R$^c$ may each independently be a substituted or unsubstituted group selected from hydrogen, an alkyl group, an alkylene group, an aryl group, an arylalkyl group, a cycloalkyl group, a heterocyclyl group, a heteroaryl group, and a heteroarylalkyl group, or may combine to form a 3 to 7 membered ring having 0 to 2 heteroatoms.

In some embodiments, the modified-NTP used in the method of the present inventive concept may have any one of the following formulae 1 to 6.

formula 1

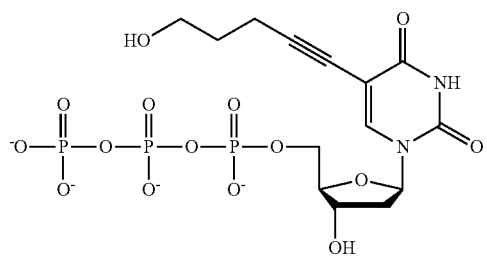

formula 2

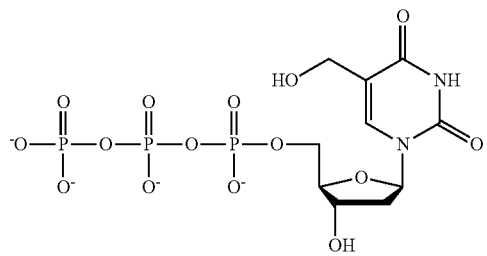

formula 3

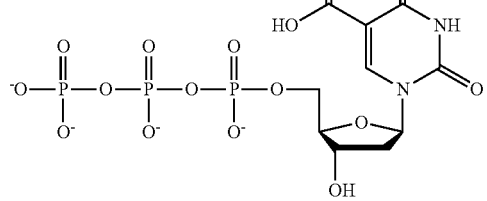

formula 4

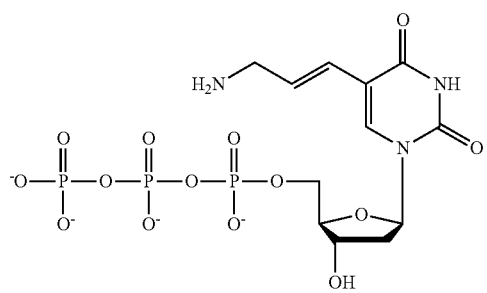

formula 5

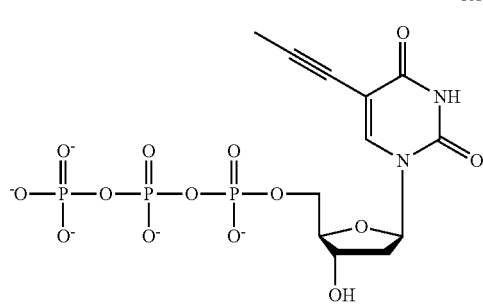

formula 6

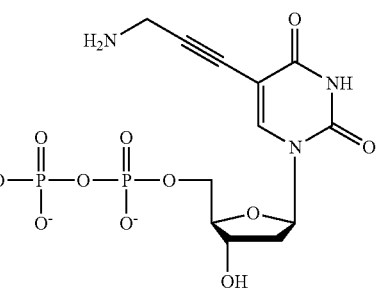

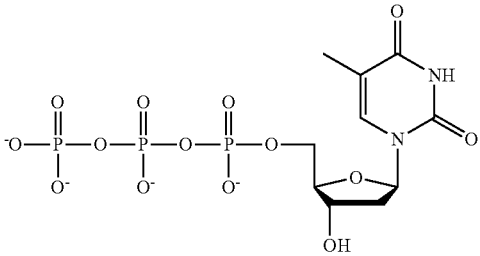

Unmodified dTTP

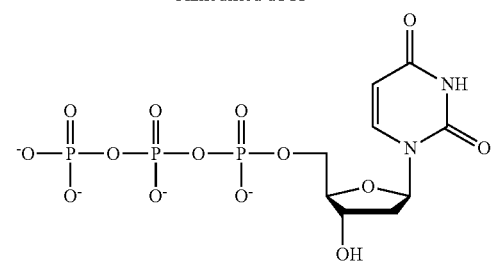

Unmodified dUTP

All the formulae 1 to 6 represent modified forms of dTTP and dUTP (the unmodified formula, as examples of naturally occurring NTP), and in the present inventive concept, the modified-dUTP having Chemical formula 1 may be designated as 5-HP(5-Hydroxypentynyl-2'-deoxyuridine-5'-Triphosphate), the modified-dUTP having formula 2 may be designated as 5-HM(5-Hydroxymethyl-2'-deoxyuridine-5'-Triphosphate), the modified-dUTP having formula 3 may be designated as 5-CA(5-carboxy-2'-deoxyuridine-5'-triphosphate), the modified-dUTP having formula 4 may be designated as 5-AA(5-Aminoallyl-2'-deoxyuridine-5'-Triphosphate), the modified-dUTP having formula 5 may be designated as 5-PP(5-Propynyl-2'deoxyuridine-5'-Triphosphate), and the modified-dUTP having formula 6 may be designated as 5-PA(5-Propargylamino-2'-deoxyuridine-5'-Triphosphate). Also, the modified-dUTP may refer to the modified-dTTP.

In the extending of the primer, the incubation may be a polymerase reaction, and the polymerase reaction may be selected from primer extension, rolling circle amplification, rolling circle transcription, in vitro transcription, polymerase chain reaction, and nucleotide terminal transferase reaction.

The term 'primer extension' refers to a technique of mapping the 5'-end of RNA, whereby DNA is synthesized by reverse transcriptase from a primer capable of complementarily binding to RNA. For example, when the template nucleotide is RNA, primer extension may be used. In some embodiments, when RNA is mRNA, a polynucleotide produced by primer extension may be cDNA.

The term 'rolling circle amplification', also called RCA, refers to a technique of continuously amplifying a template DNA by isothermal polymerization using single-stranded circular DNA as the template and a primer complementary thereto. In some embodiments, when the method of amplifying polynucleotides requires a template nucleotide chain which is optimized for the RCA reaction, the method may further comprise extending a primer by incubating a reaction mixture containing a template for the preparation of the circular template chain for the RCA reaction, the primer complementary to the template, a ligation buffer, and T4 DNA ligase.

The term 'rolling circle transcription (RCT)' refers to a technique of continuously synthesizing and amplifying RNA complementary to circular DNA by isothermal polymerization using the single-stranded circular DNA as a template and a primer complementary thereto. T7 and E. coli RNA polymerase may be used for the synthesizing.

The term 'in vitro transcription' refers to a technique of synthesizing RNA from a DNA template in vitro, and in vitro transcription may be used to produce RNA (e.g., radiolabeled RNA probe) to be used in a blot hybridization assay, a nuclease protection assay, etc. In some embodiments, in vitro transcription requires incubating a reaction mixture containing a purified DNA template containing a promoter sequence, NTP (particularly, ribonucleotide triphosphate), a reaction buffer, and an appropriate phage RNA polymerase, and the incubation conditions may vary depending on a quantity of desired RNA, a nucleotide sequence, and structural characteristics, etc.

The term 'polymerase chain reaction (PCR)' refers to a technique of amplifying a polynucleotide from a primer using DNA as a template and the primer being complementary thereto, and for example, may comprise denaturing DNA to separate double-stranded DNA into single-stranded DNA; binding the template nucleotide with a primer which is at least partially complementary to the template nucleotide; and extending the primer by Taq polymerase. However, each step and reaction conditions may vary depending on a type of PCR.

The term 'nucleotide terminal transferase reaction' is a reaction involving terminal deoxynucleotidyl transferase which is a DNA polymerase expressed in immature, pre-B, and pre-T lymphoid cells, whereby a nucleotide sequence is extended from the 3'-end. For example, when a nucleotide terminal transferase reaction is employed in antibody genetic recombination, N-nucleotide may be bound to V, D, and J exons of TCR and BCR.

In some embodiments, the polynucleotide may be selected from the group consisting of genomic DNA, an antisense oligonucleotide, mRNA, siRNA, micro-RNA, sgRNA, and an aptamer. According to a desired polynucleotide among the polynucleotides, incubation conditions or a kind of polymerase reaction may vary. The term 'genomic DNA' refers to DNA found in the genome, and may include all DNA before and after splicing. The term 'mRNA' refers to RNA which serves as a template strand during translation for polypeptide production. The term 'siRNA (small interfering RNA)' may be used interchangeably with short interfering RNA or silencing RNA, and siRNA interferes with expression of a specific gene having a nucleotide sequence complementary to the siRNA in an RNA interference pathway. The term 'sgRNA (single-stranded guide RNA)' refers to RNA which acts together with a Cas9 system to recognize DNA having a sequence complementary to a nucleotide sequence of sgRNA, leading to cleavage or degradation of the DNA. The term 'aptamer' refers to single-stranded DNA or RNA having high specificity and affinity for a particular target substance.

The method of preparing nanoparticle-type polynucleotides of the present inventive may be for packing the polynucleotides.

The term 'packing' refers to a procedure that enables polynucleotides to exist in a predetermined range of size or shape. Polynucleotides produced by a general amplification reaction form a linear shape, a shape like a loose ball of yarn, or an atypical spongy structure (a shape, in which a fibrillar skeleton forms a large number of fine pores), whereas packed polynucleotides may form, for example, a shape like a ball of yarn with high density or a relatively spherical shape, as compared with a product of the general amplification reaction, and therefore, packed polynucleotides may have a smaller surface area. For example, referring to FIG. 3B, when RCA is performed using nucleotides comprising 5-allylamino-dUTP (105.71±4.79 nm, when the modified-NTP is 20%), which is one example of modified-NTPs, products are aggregated so as to have a smaller size and to have a smaller surface area than products obtained by using only unmodified NTP (190.13±2.97 nm, when the modified-NTP is 0%).

This packing may occur naturally, without external manipulation or another cofactor, but by a particular nucleotide sequence in the produced polynucleotide or the nucleotide sequence including nucleotides derived from modified-NTPs. For example, if the polynucleotide has a particular nucleotide sequence capable of forming a hairpin structure or an aptamer structure, the polynucleotide produced by polymerase may form the particular structure by a hydrogen bond or an ionic bond. For example, if the polynucleotide has a nucleotide sequence including nucleotides derived from modified-NTPs having a stronger positive charge than natural NTP (if 5-allylamino-dUTP is used as modified-NTP, however, a ratio of NTP or a property of the residue applied to modification of NTP may influence), an ionic bond is formed between the polynucleotide having a negative charge induced by the phosphate group of NTP and the modified-NTP having a positive charge, leading to spontaneous packing of the polynucleotide.

However, this packing may include increasing a surface area or forming a particular nucleotide structure according to a purpose of the packing. Therefore, the kind of modified-NTP to be selected, a ratio of modified-NTP to the total NTP, a ratio of each of modified-ATP, modified-TTP (that is, modified-m$^5$UTP), modified-CTP, modified-GTP, and modified-UTP to total modified-NTP, the modification method, the nucleotide sequences, etc. may vary depending on the purpose of the packing.

In some embodiments, the polynucleotide may include at least partially a nucleotide sequence forming a biomolecular structure. The term 'biomolecular structure' means a three-dimensional structure formed by intricate folding of DNA, RNA, or a protein. The biomolecular structure may include a secondary structure, a tertiary structure, a quaternary structure, or a combination thereof. The term 'secondary structure' means a three-dimensional shape of local segments of polynucleotides formed by interaction between nucleotide bases. Particularly, the secondary structure may include tetraloops, pseudoknots, stem-loops, hairpins, etc., but is not limited thereto. The term 'tertiary structure' means a structure that can carry out functions in a living body, and particularly, a structure that is enzymatically recognized, but is not limited thereto. The term 'quaternary structure' means an arrangement of multiple subunits. Particularly, the quaternary structure may include a structure formed by interactions between DNA and histones or between RNA and ribosomes, but is not limited thereto. In some embodiments, to prepare polynucleotides in the form of desired nanoparticles, the polynucleotides may be manipulated to include a combination of modified nucleotides and nucleotide sequences capable of forming the biomolecular structure.

In some embodiments, the packing may be for controlling the surface area of the polynucleotides. Further, the packing may be for storing the polynucleotides or controlling transfection of the polynucleotides. After incubation of the reaction mixture, inorganic salts remaining in the reaction mixture or polynucleotides produced by enzymatic action may be degraded or degenerated, and even though the produced polynucleotides are stored in a purified buffer solution, the polynucleotides may be gradually degraded or denatured for long-term storage. However, when the produced polynucleotides are spontaneously packed due to a particular nucleotide sequence in the polynucleotides, particularly, by interactions between nucleotide sequences caused by modified-NTPs, their surface area may be decreased, and therefore, the packed polynucleotides may be less influenced by the inorganic salts or enzymatic action than unpacked polynucleotides. Accordingly, it is possible to store the desired polynucleotides more stably, and in another embodiment, the polynucleotides may be advantageous in terms of long-term storage. Further, depending on a storage environment of the polynucleotides, a ratio of modified-NTP to the total NTP in the polynucleotide or the kind of the modified-NTP may vary.

Further, since the produced polynucleotides may exist in a linear form or in a size inadequate to pass through cell membranes, an appropriate transfection reagent may be needed in order to transfer the polynucleotides into cells. However, the properly packed polynucleotides may have a suitable form and size to pass through cell membranes, and therefore, they may be transferred into cells without transfection reagents. Consequently, cytotoxicity of a reagent used for transfection may be avoided by using the packed polynucleotides which can be packed. In another embodiment, to increase intracellular delivery of the packed polynucleotides, they may be transfected in combination with a transfection reagent.

Another aspect of the present invention provides a composition comprising polynucleotides produced by the method comprising extending the primer by incubating the reaction mixture containing the template nucleotide, the polymerase, modified-NTP (nucleoside triphosphate), and the primer having a sequence at least partially complementary to the template; and amplifying the polynucleotides at least partially comprising the modified nucleotides, in which the modified-NTP may comprise modified forms of one or more selected from the group consisting of ATP, TTP, CTP, GTP, and UTP. The composition may be for stably storing the polynucleotides or for transfecting the polynucleotides. Therefore, the composition may include, for example, appropriate inorganic salts or compounds for long-term storage. Further, the composition may include, for example, an appropriate amount of a transfection reagent to facilitate transfection.

In some embodiments, the polynucleotide may be linear or circular.

In another embodiment, the polynucleotide may be a composition at least partially including modified-NTP. In the polynucleotide, an appropriate amount of the modified-NTP may exist together with NTPs at a particular proportion. For example, the modified-NTP may be used at a proportion of 10%, 20%, 50%, 80%, or 100% with respect to the total NTPs in the method of amplifying the polynucleotide. Therefore, the produced polynucleotide may also include the modified-NTP at a proportion of 10%, 20%, 50%, 80%, or 100% with respect to the total NTPs according to the proportion of the modified-NTP used. These proportions may be determined according to each NTP (that is, a proportion of each of modified-ATP, -TTP, -CTP, -GTP, and -UTP to ATP, TTP, CTP, GTP, and UTP).

Still another aspect of the present invention provides a nucleotide packing kit containing NTPs to be used in the method, the NTPs at least partially comprising modified-NTPs.

The kit may be provided in the form of a kit comprising a packaging unit having one or more reaction reagents. Further, the kit may contain one or more of the following items: a buffer solution, an instruction manual, a template nucleotide, a primer having a sequence at least partially complementary to the template, a polymerase, NTPs, and modified-NTPs. The kit may include containers of the reaction reagents to be mixed at an appropriate ratio in order to perform the method described in the present inventive concept. A reagent container may include a unit quantity of the reaction reagent so that measuring may be omitted when the method is carried out. In another embodiment, the kit reagent may further include a reagent to purify polynucleotides produced from reaction products. Further, the kit reagent may include a reagent to quantify, qualify, or detect the produced polynucleotides.

According to an aspect of the present invention, a method of amplifying polynucleotides at least partially comprising modified-NTPs may be used to produce polynucleotides which are spontaneously packed, wherein the method comprises extending a primer by incubating a reaction mixture comprising a template nucleotide, a polymerase, modified-NTPs (nucleoside triphosphates), and the primer having a sequence at least partially complementary to the template, in which the modified-NTPs may include modified forms of one or more selected from the group consisting of ATP, TTP CTP, GTP, and UTP.

According to another aspect of the present invention, a composition comprising the polynucleotides produced by the above method enables long-term storage of the produced polynucleotide or may increase intracellular transfection efficiency of the polynucleotide.

According to still another aspect of the present invention, a nucleotide packing kit comprising NTPs to be used in the above method, the NPTs at least partially comprising modified-NTPs, may be used to produce polynucleotides that are spontaneously packed for long-term storage or high transfection efficiency.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects.

Hereinafter, the present inventive concept will be described in more detail with reference to Examples. However, these Examples are provided for illustrative purposes only, and the scope of the invention is not intended to be limited by these Examples.

Example 1: Verification of Polynucleotide Packing Effect

In this Example, packing effects of polynucleotides produced by RCA reactions were examined.

1. Production of Polynucleotides by RCA Reactions

(1) Preparation of Circular Template Chain for RCA Reaction

All DNA oligonucleotides were purchased from Bioneer (Korea, Daejeon). Templates T1, T2, and T3 phosphorylated at the 5'-end were mixed with a primer having a sequence as in the following Table 1, a ligation buffer, and T4 DNA ligase, and incubated at 16° C. overnight. After ligation, circular template chain products were separated by 10%-denaturing polyacrylamide gel electrophoresis, and purified by ethanol precipitation.

The primer used in the above reaction and nucleotide sequences of the templates and products are described in the following Table 1 (primer binding sites in the templates are underlined, and aptamer sequences in P2 and P3 are indicated in bold).

TABLE 1

| Primer | | Sequence (5'→3')<br>CTCTGGTGAGGACAGGACTT |
|---|---|---|
| Sequences of template and product | T1 | CTCACCAGAGAAAAAAAAAAAAAAAAAAAAAAAAAAAAAAAAAA<br>AAAAAAAAAAAAAAAAAAAAAAAAAAAGTCCTGTC |
| | P1 | (GACAGGACTTTTTTTTTTTTTTTTTTTTTTTTTTTTTTTT<br>TTTTTTTTTTTTTTTTTTTTTTTTTCTCTGGTGAG)n |
| | T2 | CTCACCAGAGCCGCATGCCATCCGCCCAGTTGACAAAAAAA<br>CCGCATGCCATCCGCCCAGTTGACAAGTCCTGTC |
| | P2 | (GACAGGACTTGTCAACTGGGCGGATGGCATGCGGTTTTTTT<br>GTCAACTGGGCGGATGGCATGCGGCTCTGGTGAG)n |
| | T3 | CTCACCAGAGCCACCACCACCAACACCACCACCACCAAAAA<br>AACCACCACCACCAACACCACCACCACCAAGTCCTGTC |
| | P3 | (GACAGGACTTGGTGGTGGTGGTGTTGGTGGTGGTGGTTTTT<br>TTGGTGGTGGTGGTGTTGGTGGTGGTGGCTCTGGTGA G)n |

In Table 1, of the RCA products, P1, P2, and P3 which were produced from circular template chains, T1, T2, and T3, respectively, P1 has a sequence of simple thymine repeats, whereas P2 and P3 include MUC1 and AS1411 aptamer sequences capable of forming secondary structures in their sequences, respectively.

(2) RCA Reaction

Reaction buffers containing the circular template chains, dNTP, the primer, and phi29 DNA polymerase was incubated at 37° C. for 1 hour. To incorporate modified-NTP, modified-dUTP modified at the 5-carbon site was mixed with dTTP in various proportions (the proportion of modified-NTP relative to the sum of NTPs and modified-NTP was 0%, 20%, 50%, 80%, or 100%). 5-HP(5-Hydroxypentynyl-2'-deoxyuridine-5'-Triphosphate) was kindly provided by Dr. Marcel Hollenstein (Pasteur Institut, Paris, France). 5-HM(5-Hydroxymethyl-2'-deoxyuridine-5'-Triphosphate), 5-CA(5-Carboxy-2'-deoxyuridine-5'-Triphosphate), 5-AA (5-Aminoallyl-2'-deoxyuridine-5'-Triphosphate), 5-PP(5-Propynyl-2'deoxyuridine-5'-Triphosphate), and 5-PA(5-Propargylamino-2'-deoxyuridine-5'-Triphosphate) were purchased from TriLink Biotechnologies (San Diego, USA) and used as the modified-NTP. Next, the reaction products were incubated at 65° C. for 10 minutes to inactivate the polymerase.

2. Packing Effects of Polynucleotides Produced by RCA Reactions

(1) Agarose Gel Electrophoresis

In order to examine whether RCA products were produced in an amount sufficient enough to measure the sizes of the polynucleotides, the products were electrophoresed on an agarose gel.

The products obtained by RCA reaction were subjected to electrophoresis on a 0.5% agarose gel using a 0.5×TBE solution at 100 V for 45 minutes at 25° C. The electrophoresed gel was stained with SYBR gold, and images were obtained by a fluorescence scanner (GelDoc, DNR, Israel).

It was confirmed that all of P1, P2, and P3 were produced by RCA reaction in an amount sufficient enough to measure the sizes of the polynucleotides. For the RCA reaction using modified-NTP, a mixture of dNTPs and 5-allylamino-dUTP which is a form of modified-NTP of dUTP was used, and when there was 100% replacement of dTTP with 5-allylamino-dUTP, the amount of RCA products produced was not enough (data not shown). However, when there was 80%, 50%, or 20% replacement of dTTP with 5-allylamino-dUTP, RCA products were produced in an amount sufficient enough to measure the sizes of the polynucleotides. In contrast, when modified-NTP 5-HM, 5-CA, 5-AA, 5-PP, 5-PA, and 5-HP were used, all 6 modified-NTPs were employed in RCA reactions, and thus polynucleotides were produced in an amount sufficient enough to measure their sizes.

(2) Dynamic Light Scattering (DLS) Analysis

In order to analyze whether the specific nucleotide sequences of RCA products influence packing to cause changes in sizes of polynucleotides, dynamic light scattering was measured.

Hydrodynamic sizes of the RCA products were measured using a Zetasizer (Malvern, UK). A concentration of the samples for DLS analysis was 150 nM.

Figure 2A:
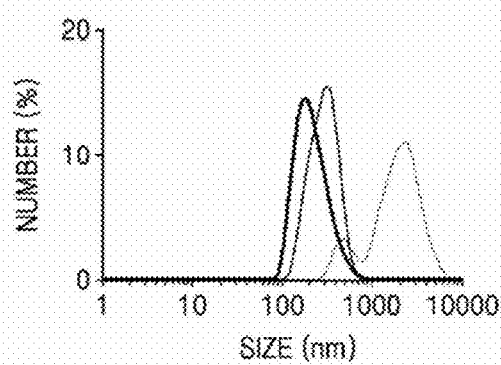
FIG. 2A shows results of dynamic light scattering (DLS) analysis showing hydrodynamic sizes of rolling circle amplification (RCA) products (P1 (the most thin line) and P3 (the most bold line))

As a result, referring to FIG. 2A, P2 and P3 had nucleotide sequences capable of forming secondary structures in their sequences, unlike P1, and P2 and P3 had stronger self-assembly ability than P1, and were therefore well packed. As a result, the obtained polynucleotides had smaller sizes, with P3 showing the most compact packing. Furthermore, in the size distribution, P2 and P3 which were expected to have particular structures showed uniform size distribution, as compared with P1. This packing results from the sequences of the nucleotides used themselves.

Figure 3A:
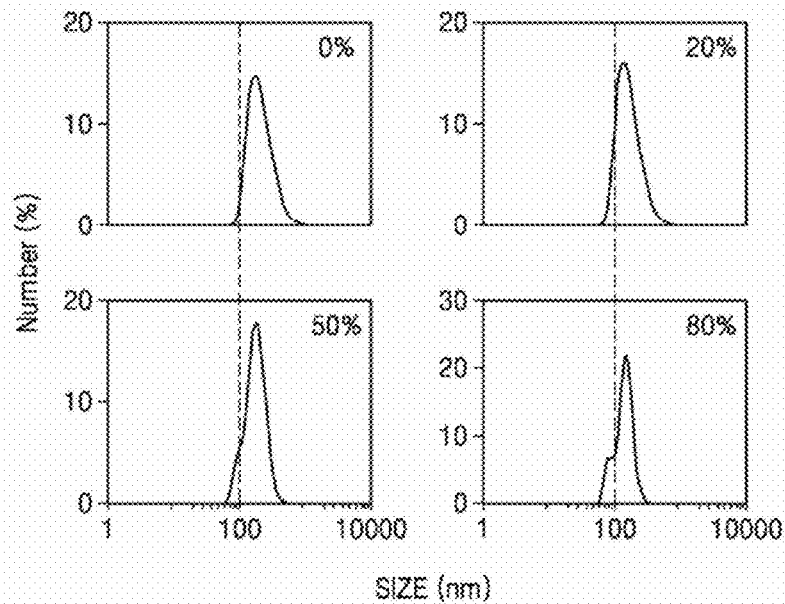
FIG. 3A shows results of DLS analysis showing hydrodynamic sizes of 5-aminoallyl-dUTP-incorporated RCA products obtained at various concentrations of 5-aminoallyl-dUTP.

For another different packaging level in addition to the above results, 5-allylamino-dUTP which is a modified-NTP of dUTP was mixed with dNTPs and used in an RCA reaction. As shown in FIG. 3A, it was confirmed that when the polymerization reaction was performed using a mixture of 5-allylamino-dUTP and dNTP, the sizes of the produced nucleotides were controlled to be smaller than those of nucleotides produced by a polymerization reaction using only dNTP.

Figure 4A:
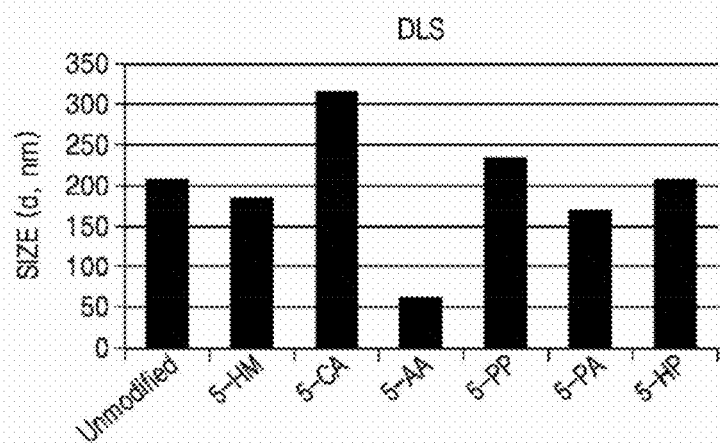
FIG. 4A shows results of DLS analysis showing hydrodynamic sizes of RCA products obtained according to the kind of modified-NTPs which were used in the RCA reactions.

Based on this result, many different modified-NTPs, that is, 5-HM, 5-CA, 5-AA, 5-PP, 5-PA, and 5-HP (20% of dTTP was replaced therewith) were used in RCA reactions, and as confirmed in FIG. 4A, the packaging levels of the produced polynucleotides were found to be associated with chemical properties of the residues used in the modification of the used nucleotides. The polynucleotides obtained by incorporation of 5-CA having a negatively charged residue had increased sizes, as compared with products into which no modified-NTPs were incorporated. The polynucleotides produced by incorporation of 5-AA and 5-PA having positively charged residues had decreased sizes. Incorporation of 5-HM and 5-HP which are able to form hydrogen bonds but have neutral residues did not greatly change the sizes of nucleotide products. Incorporation of 5-PP having a hydrophobic neutral residue slightly increased the size of products. Therefore, it can be seen that packaging levels of polynucleotides may vary depending on the secondary structures produced by the nucleotide sequences themselves, and a specific charge or binding property of modified-NTPs influences the packing.

(3) Atomic Force Microscopy

To visualize the packing effects caused by nucleotide sequence specificity and modified-NTPs, the sizes of the RCA products were measured by atomic force microscopy.

For atomic force microscopy, the RCA products were deposited on mica, and 1 hour later, the surface of the mica was washed with distilled water, and immediately dried with nitrogen gas. The samples were scanned on Park XE-100 (Park System Corp. Korea) AFM in non-contact mode with PPP-NCHR tip (Park System Corp. Korea). AFM images were analyzed using XEI 4.1.0 software.

Figure 2B:
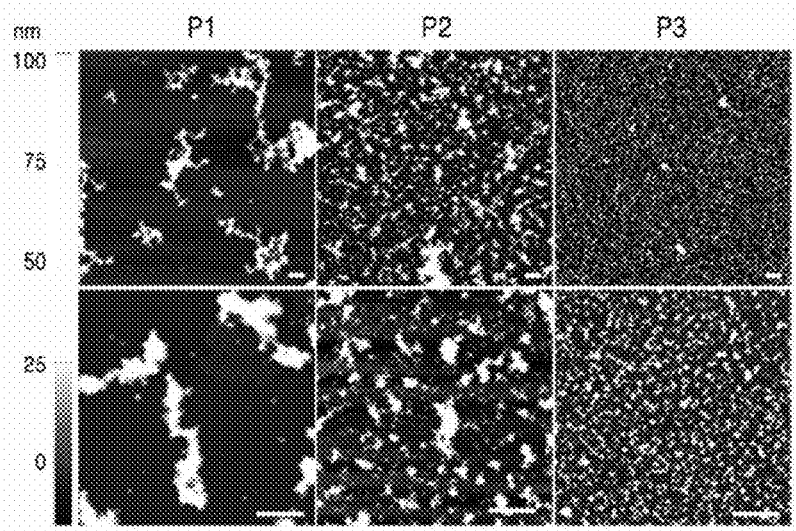
FIG. 2B shows atomic-force microscopy (AFM) images of the RCA products.

As shown in FIG. 2B, it was confirmed that the polynucleotide sizes of P2 and P3 were much smaller and more uniform than that of P1, and the size of P3 was the smallest.

Figure 3B:
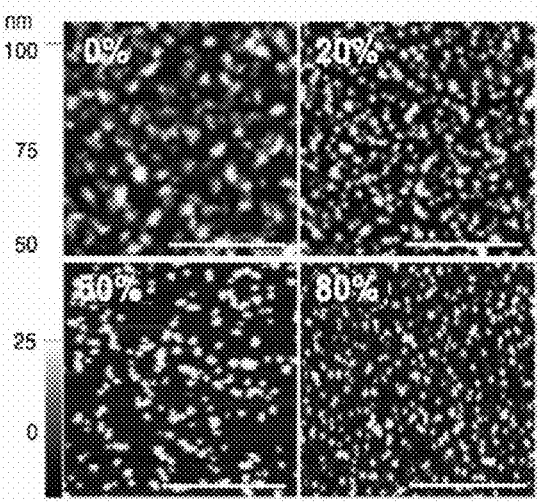
FIG. 3B shows AFM images of the RCA products.

Likewise, as shown in FIG. 3B, when a mixture of dNTPs and 5-allylamino-dUTP which is a modified-NTP was used in an RCA reaction, the produced polynucleotides were well packed and thus their sizes were smaller and their shapes maintained as more uniform than those of nucleotides produced by polymerization reaction using only dNTP.

Figure 4B:
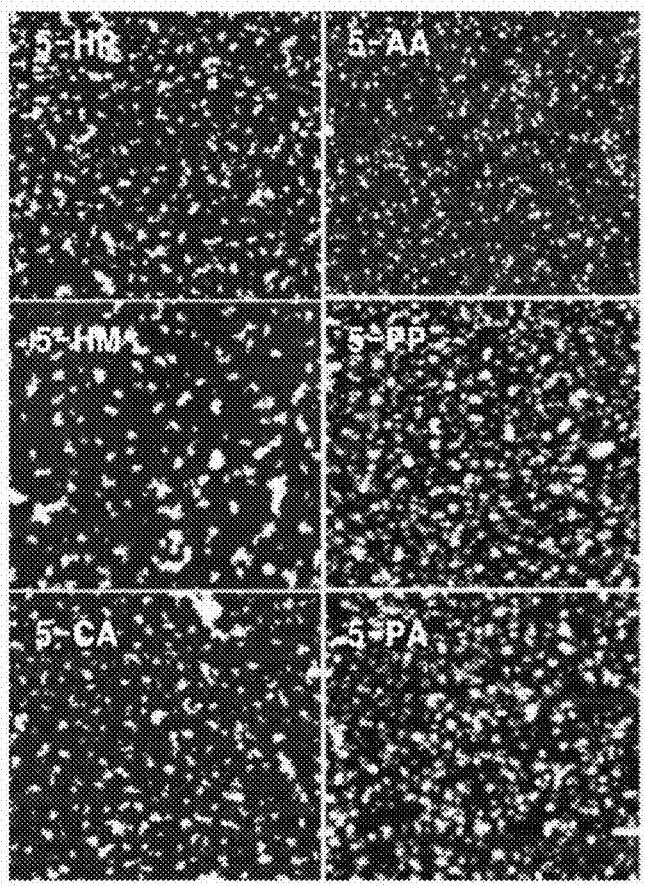
FIG. 4B shows AFM images of the RCA product obtained according to the kind of modified-NTPs.

With regard to polynucleotides incorporated with the modified-NTPs, 5-HM, 5-CA, 5-AA, 5-PP, 5-PA, and 5-HP (20% of dTTP was replaced therewith), as confirmed in FIG. 4B, polynucleotides produced by incorporation of 5-AA and 5-PA having positively charged residues showed relatively uniform sizes, as compared with those produced by incorporation of 5-CA having a negatively charged residue or 5-PP having a hydrophobic neutral residue. In particular, it can be seen that the polynucleotides produced by 5-AA had small and uniform sizes. These results are consistent with the results of DLS analysis, and indicate that a specific charge or binding property of modified-NTPs influences the packing of polynucleotides.

Example 2: Verification of Intracellular Delivery Efficiency of Packed Polynucleotides In this Example, it was examined whether intracellular delivery efficiency is increased by packing of the polynucleotides produced by RCA reactions using modified-NTPs.

1. Intracellular Transfection of Packed Polynucleotides

HeLa cells were seeded in a 35 mm glass-bottom Petri dish containing DMEM medium (Gibco, USA) supplemented with 10% heat-inactivated fetal bovine serum, 1% penicillin, and streptomycin. $2.5 \times 10^4$ cells were seeded on each dish, and incubated overnight at 37° C. in a humid atmosphere of 5% $CO_2$. The growth medium was removed from each cell sample, and cells were washed with PBS (Gibco, USA) twice. The RCA products, packed polynucleotides in a fresh serum- and antibiotic-free medium (250 µl), were added to the cell samples, and incubated at 37° C. in a humid atmosphere of 5% $CO_2$ for 6 hours.

2. Verification of Intracellular Delivery Efficiency of Polynucleotides (1) Fluorescence Microscopy In order to measure the amount of the polynucleotides delivered into cells, cells were treated with the polynucleotides produced by RCA reactions, and then observed.

In detail, for microscopy, a Cy5-labeled primer and modified-NTPs, 5-HM, 5-CA, 5-AA, 5-PP, 5-PA, and 5-HP were used to perform RCA reactions as described above to prepare packed nucleotide products. Cell nuclei were stained with Hoechst 34580 (3 µg/mL, Invitrogen, USA) and washed with PBS (200 µl) twice. Next, a cell culture medium (200 µl) was added thereto. Live cells were imaged using fluorescence microscopy (LMS 700, Carl Zeiss Microscopy, Germany). Excitation/emission filters used for Cy5 and Hoechst 34580 were 630-650/665-705 nm, and 340-380/432-482 nm, respectively.

Figure 5A:
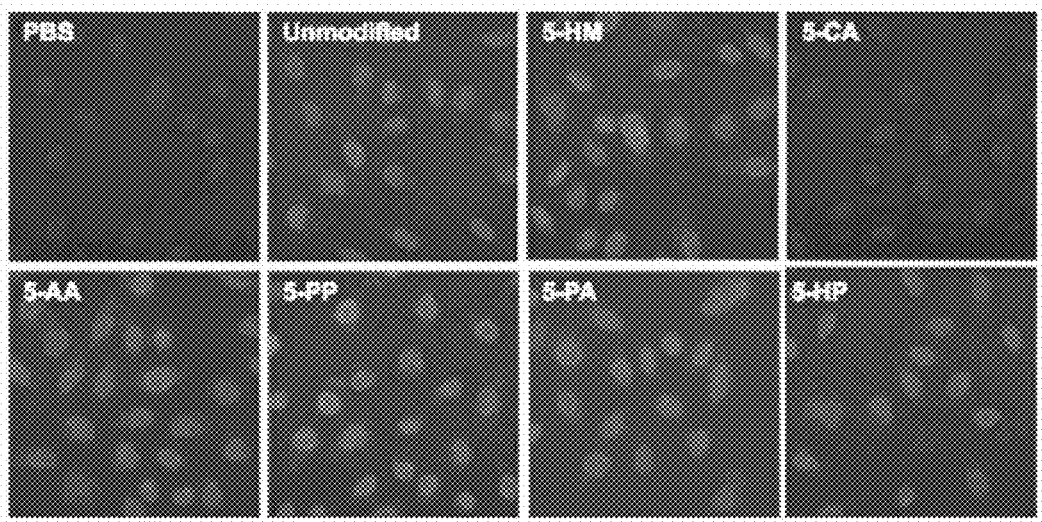
FIG. 5A shows fluorescence microscope images of cellular uptake of the polynucleotides produced from the different kinds of modified-NTPs which were used in RCA reactions, and FIG. 5B show results of cellular uptake measured by flow cytometry.

As shown in FIG. 5A, the polynucleotides obtained by incorporation of 5-CA having a negatively charged residue and 5-PP having a hydrophobic neutral residue were able to form hydrogen bonds, but the amounts of the polynucleotides delivered into cells were smaller than those of the polynucleotides obtained by incorporation of 5-HM and 5-HP having neutral residues, and the polynucleotides showed a remarkable difference from those of the polynucleotides obtained by incorporation of 5-AA and 5-PA having positively charged residues. These results are consistent with the results of the AFM analysis, and indicate that the packing of polynucleotides also influences intracellular delivery efficiency of the polynucleotides.

(2) Flow Cytometry

For flow cytometry, HeLa cells were seeded at a density of $1 \times 10^5$ cells/mL on 12-well plates and incubated for 24 hours, and then washed with PBS twice. As in the fluorescence microscopy, the cells were incubated with the packed polynucleotides produced by RCA reactions using a Cy5-labeled primer, and harvested and washed three times with PBS. Then, 0.2 mL of trypsin replacement (TrypLE™, Gibco, USA) was added to each sample, and the samples were incubated for 5 min at 37° C. Then, 1 mL of media was added to each sample, and the resulting cell suspensions were transferred to conical tubes (Falcon™ tubes, BD Biosciences, USA) and centrifuged for 3 minutes at 2500 rpm. Supernatant was discarded, and the cell pellets were resuspended in 1 mL of PBS. Cy5 intensity of the cells was determined by flow cytometry (Guava, Millipore, USA). Samples of at least 10,000 cells were analyzed in triplicate.

Figure 5B:
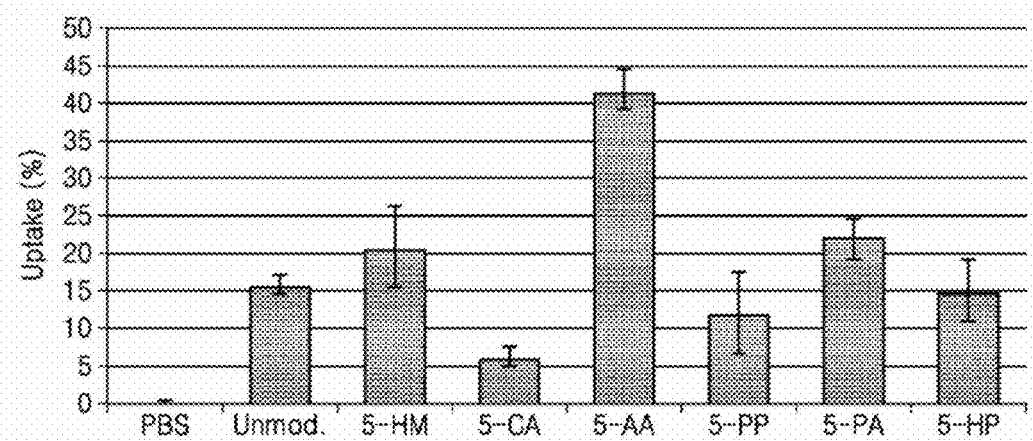

As shown in FIG. 5B, it was confirmed that well-packed polynucleotides were readily delivered into cells. When the size of the packed structure was smaller, higher delivery efficiency was observed, indicating that size control by packing of polynucleotides having a biochemical activity prepared in vitro may be applied in a highly efficient method of delivering the polynucleotides.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims.

What is claimed is:

1. A method of preparing nanoparticle polynucleotides, the method comprising forming the polynucleotides comprising modified nucleotides, wherein the forming comprises chemically synthesizing the polynucleotides comprising modified nucleotides, synthesizing the polynucleotides comprising modified nucleotides using an enzyme, or a combination thereof, and wherein the polynucleotides comprise at least partially a nucleotide sequence forming a secondary structure, a tertiary structure, a quaternary structure, or a combination thereof as a biomolecular structure, wherein the modified nucleotides have a modification of the hydrogen of the 8-carbon site of the purine ring when a base of the modified nucleotides is adenine or guanine, of the hydrogen of the 5-carbon site of the pyrimidine ring when a base of the modified nucleotides is cytosine or uracil, and of the methyl group of the 5-carbon site of the pyrimidine ring when a base of the modified nucleotides is thymine, the modified nucleotides being modified by substituting the hydrogen or the methyl group with a cationic residue.

2. The method of claim 1, wherein the nanoparticle polynucleotides are self-assembled.

3. The method of claim 1, wherein the chemically synthesizing the polynucleotides comprising modified nucleotides comprises synthesizing by oligo nucleotides synthesis.

4. The method of claim 1, wherein the synthesizing the polynucleotides comprising modified nucleotides using an enzyme comprises the steps of extending a primer by incubating a reaction mixture comprising a template nucleotide, a polymerase, modified-NTPs (nucleoside triphosphates), and the primer having a sequence at least partially complementary to the template; and amplifying polynucleotides at least partially comprising the modified nucleotides, wherein the modified-NTPs are one or more selected from the group consisting of modified-ATP, modified-TTP, modified-CTP, modified-GTP, and modified-UTP.

5. The method of claim 4, wherein the modified-NTPs are dNTPs (deoxyribonucleoside triphosphates) or rNTPs (ribonucleoside triphosphates).

6. The method of claim 4, wherein the template nucleotide is DNA or RNA.

7. The method of claim 4, wherein the template nucleotide is single-stranded or double-stranded.

8. The method of claim 4, wherein the template nucleotide is circular or linear.

9. The method of claim 1, wherein the modified nucleotides have a modification of one or more of a five-carbon sugar, a phosphate group, and a base.

10. The method of claim 1, wherein the cationic residue is a substituted $C_1$-$C_{30}$ alkyl group, a substituted $C_2$-$C_{30}$ alkenyl group, a substituted $C_2$-$C_{30}$ alkynyl group, a substituted $C_3$-$C_{30}$ cycloalkyl group, a substituted $C_5$-$C_{30}$ aryl group, a substituted $C_5$-$C_{30}$ arylalkyl group, a substituted $C_5$-$C_{30}$ arylalkenyl group, a substituted $C_5$-$C_{30}$ arylalkynyl group, a substituted $C_5$-$C_{30}$ heteroaryl group, a substituted $C_3$-$C_{30}$ heterocyclyl group, a substituted $C_3$-$C_{30}$ heterocycloalkyl group, a substituted $C_3$-$C_{30}$ heterocyclylalkyl group, a substituted $C_5$-$C_{30}$ heteroarylalkyl group, a substituted $C_5$-$C_{30}$ heteroarylalkenyl group, or a substituted $C_5$-$C_{30}$ heteroarylalkynyl group, which is substituted with one or more selected from the group consisting of an amine, guanidine, pyridine, and imidazole.

11. The method of claim 1, wherein the modified nucleotides are derived from nucleotides which have any one chemical formula of the following Formulae 4 or 6:

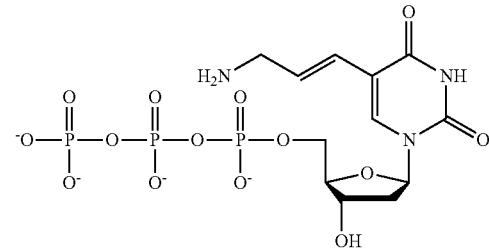

formula 4

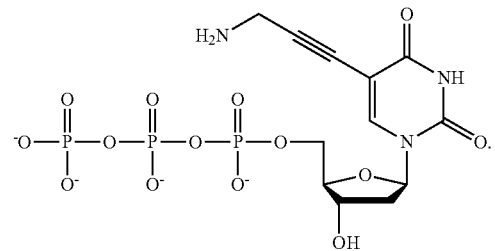

formula 6

12. The method of claim 1, wherein the polynucleotides are selected from the group consisting of genomic DNA, antisense oligonucleotides, mRNA, siRNA, micro RNA, sgRNA, and aptamers.

13. The method of claim 1, wherein the method is used for controlling a surface area of the polynucleotides, used for storing the polynucleotides, or used for controlling transfection of the polynucleotides in cells, wherein
- controlling the surface area of the polynucleotides is carried out by interacting between nucleotide sequences caused by modified-NTPs,
- storing the polynucleotides is carried out for long-term storage, and
- controlling transfection of the polynucleotides is carried out by passing the polynucleotides through cell membrane into cells without transfection reagents.

* * * * *